United States Patent [19]

Bailliard et al.

[11] Patent Number: 5,126,485
[45] Date of Patent: Jun. 30, 1992

[54] PROCESS FOR THE HYDROGENATION OF HALOGENONITRO-AROMATIC COMPOUNDS IN THE PRESENCE OF A SULFUR-CONTAINING COMPOUND

[75] Inventors: Rosemarie Bailliard, Lyons; Georges Cordier; Jean-Michel Grosselin, both of Francheville; Bernard Langlois, Lyons; Laurent Gilbert, Lyons; Gerard Forat, Lyons, all of France

[73] Assignee: Rhone-Poulenc Chimie, Cedex, France

[21] Appl. No.: 554,515

[22] Filed: Jul. 20, 1990

[30] Foreign Application Priority Data

Jul. 20, 1989 [FR] France ................ 89 09766

[51] Int. Cl.⁵ .................................... C07C 209/36
[52] U.S. Cl. ................. 564/416; 564/414; 564/415
[58] Field of Search ............ 564/416, 417, 415

[56] References Cited

U.S. PATENT DOCUMENTS

| | | | |
|---|---|---|---|
| 3,637,820 | 1/1972 | Dodman et al. | 564/416 |
| 4,059,627 | 11/1977 | Kritzler et al. | 564/417 |
| 4,115,652 | 9/1978 | Linhart et al. | 564/417 |
| 4,215,226 | 7/1980 | Onopchenko et al. | 564/423 |

FOREIGN PATENT DOCUMENTS 57-65349 12/1982 Japan ............................ 564/416

*Primary Examiner*—Glennon H. Hollrah
*Assistant Examiner*—Shailendra Kumar
*Attorney, Agent, or Firm*—Finnegan, Henderson, Farabow, Garrett and Dunner

[57] ABSTRACT

A process for the hydrogenation of halogenonitroaromatic compounds wherein said compounds are contacted with a nickel-, cobalt- or iron-based catalyst, preferably Raney nickel, and hydrogen in the presence of a sulfur-containing compound. Preferably, the sulfur-containing compound is a sulfoxide or sulfone, and the molar ratio of the sulfur-containing compound to the catalyst ranges from about 1:1 to 10:1.

29 Claims, No Drawings

PROCESS FOR THE HYDROGENATION OF HALOGENONITRO-AROMATIC COMPOUNDS IN THE PRESENCE OF A SULFUR-CONTAINING COMPOUND

The present invention relates to a process for the hydrogenation of halogenated aromatic nitro compounds. It relates more particularly to the preparation of halogenated amines.

When carrying out a hydrogenation process on an aromatic nitro compound containing halogen atoms bonded to the aromatic ring, a hydrogenolysis phenomenon of the carbon-halogen bond, to give, on the one hand, the dehalogenated ring and on the other hand, hydrohalic acids, takes place at the same time as the conversion of the nitro group to an amino group.

This phenomenon has been known for a very long time as it was described in 1904 by P. Sabatier and A. Mailhe.

Numerous patents have been filed which relate to efforts to prevent this side reaction while nonetheless preserving the catalytic activity. These patents can be divided into two groups: those using Raney nickel as the hydrogenation catalyst and those using platinum or palladium. All of these patents describe the use of a modified catalyst.

The Patents U.S. Pat. No. 3,067,253, G.B. 1,191,610, J. 73-49,728, G.B. 1,498,722 and FR. 2,245,615 may be mentioned in the first group of patents which describe the use of Raney nickel.

U.S. Pat. No. 3,067,253 describes the use of Raney nickel to which calcium hydroxide or magnesium hydroxide has been added. The reaction temperatures reported are nevertheless always low (25° to 60° C.) in order to prevent dehalogenation, which makes it extremely difficult, if not impossible, to use these processes industrially.

G.B. Patent 1,191,610 describes the use of Raney nickel in combination with a thiocyanate. This process at least sometimes includes a relatively slow hydrogenation, and the catalyst is changed during the hydrogenation, which does not allow for continuous processing.

Further, the inventors consider thiocyanate to be an inorganic form of sulfur. Thus, as defined herein, the term "organic sulfur-containing compound" does not include a thiocyanate. In any event, one embodiment of the invention excludes thiocyanate and/or thiophene as the sulfur-containing compound.

Patent J. 73-49,728 describes the use of Raney nickel in combination with the presence of an alkylamine, an alkanolamine or a heterocyclic base. In this patent, the hydrogenation temperature is limited, as in the above-mentioned U.S. patent, to 60° C., which temperature does not provide a satisfactory industrial utilization since the productivity of the process at such temperature is insufficient. It is also indicated in French Patent 2,245,615 that the process of the Patent J. 73-49,728 does not allow the dehalogenation to be prevented in a satisfactory manner since at least 5% of the aniline obtained is dehalogenated.

G.B. Patent 1,498,722 describes the use of Raney nickel with a trialkyl phosphite. The reaction temperature is reported to be about 100° C., but the degree of dehalogenation varies between 2 to 8%. This process has, therefore, not been thought to be practical on an industrial scale.

The final patent recited above describing the use of Raney nickel is French Patent 2,245,615, which combines Raney nickel with a dehalogenation inhibitor chosen from dicyandiamide, cyanamide and calcium cyanamide. The temperature of the hydrogenation reaction is between 50° C. and 130° C. and the degree of dehalogenation is stated to be always below 0.15%.

French Patents 2,330,669 and 2,127,092 may be mentioned in the second group of patents describing the use of crude platinum metals. French Patent 2,330,669 describes the use of platinum deposited on charcoal and dehalogenation is inhibited by the presence of a sulfur derivative chosen from the thioethers and the disulfides as the hydrogenation catalyst for chlorinated nitro-aromatic compounds. The degree of dehalogenation is reported to be very low (0.01 to 0.08%). This low degree of dehalogenation stems largely from the platinum which, even in the absence of a sulfur derivative does not cause dehalogenation.

French Patent 2,127,092 describes the preparation of a catalyst of platinum deposited on charcoal which is sulfurized. The preparation of this catalyst consists in first carrying out a hydrogenation of the catalyst and then sulfurizing the latter by the addition of hydrogen sulfide in an amount varying between 0.45 and 0.55 mole of hydrogen sulfide per mole of absorbed hydrogen.

On the one hand, the preparation of the catalyst is difficult and, on the other hand, the use of a catalyst deposited on charcoal does not permit easy decanting from the catalytic mass. Thus it is very difficult to use the process in a continuous mode. The use of platinum, a very expensive catalyst, has caused the industry to draw back from the industrial implementation of a process of this type.

Apart from the above general problems, the more specific problems of fluorinated derivatives should be mentioned. The great majority of fluorinated anilines, whether they are fluorinated only or whether they contain (an) other halogen(s) on the aromatic ring, are prepared by exchange between the fluorine ion and a higher halogen (i.e., a halogen having a higher atomic number) from a halogenated nitro derivative.

Although this technique is one of the most satisfactory for obtaining fluorinated derivatives, it requires prior to the hydrogenation the use of high temperatures and of specific solvents, most frequently sulfones and/or sulfoxides, such as sulfolane or dimethyl sulfoxide. A large number of fluorinated derivatives, such as the difluoronitrobenzenes, are difficult to separate from this type of solvent. The corresponding aniline, however, is easy to separate.

Since the sulfur solvents ar reputed to poison the hydrogenation catalysts, it has been concluded that the fluorinated nitro derivative must be carefully purified in order to remove every trace of solvents before the hydrogenation. Moreover, the oxygenated derivatives of sulfur are relatively easy to hydrogenate to give, on the one hand, water and, on the other hand, reduced sulfur derivatives such as the thioethers.

The halogenated, and more particularly fluorinated, derivatives are very sensitive to hydrolysis during the hydrogenation, which removes two molecules of water per nitro function.

It is for this reason that one of the aims of the present invention is to provide a new process for the hydrogenation of halogenated aromatic nitro derivatives, in particular for the synthesis of halogenated anilines.

Another aim of the present invention is to provide a new process for the hydrogenation of halogenated aromatic nitro derivatives, in particular for the synthesis of halogenated amines, which surprisingly permits the use of reaction mixtures containing the chlorinated nitro derivatives and originating from exchange reactions between fluoride and a higher halogen. Yet another aim of the present invention is to provide a new process for the hydrogenation of the halogenated aromatic nitro derivatives, in particular for the synthesis of halogenated anilines, which prevents the hydrogenolysis of the carbon-halogen bonds.

The present invention can use a nickel-based catalyst, an inexpensive hydrogenation catalyst which settles easily and is therefore particularly well-suited for continuous hydrogenation, as well as cobalt- and iron-based catalysts. The catalyst, such as nickel, can be combined with a dehalogenation inhibitor to impart to the present invention all of the qualities required for the hydrogenation of halogenonitro-aromatic compounds.

The present invention comprises contacting the halogenonitro-aromatic (including polyhalogenonitro-aromatic) compound with (1) a hydrogenation catalyst consisting essentially of a metal selected from nickel, cobalt and iron, preferably nickel, and more preferably Raney nickel; (2) in the presence of a sulfur-containing compound; and (3) at a temperature and hydrogen pressure sufficient to carry out the hydrogenation, preferably wherein the molar ratio of the sulfur-containing compound to the catalyst ranges from about 1:1 to 10:1, preferably from about 5:1 to 10:1.

One group of sulfur-containing compounds which can be used includes sulfides, such as hydrogen sulfide, and sulfites, such as sulfites and hydrosulfites of alkali metals or ammonium which decompose to hydrogen sulfide in an aqueous medium. Organic sulfur-containing compounds can also be used.

The following may be mentioned by way of examples of sulfur-containing compounds which can be used:
hydrogen sulfide
sodium sulfide, potassium sulfide, ammonium sulfide
sodium hydrosulfite or sodium dithionite ($Na_2S_2O_4$)
sodium sulfite ($Na_2SO_3$)
sodium tetrathionate ($Na_2S_4O_6$)
sodium tetrasulfide ($Na_2S_4$)
thiourea
organic disulfides
sulfur-containing organic heterocyclic compounds such as thiophene or thioxane.

When it is desirable to avoid the use of large quantities of sulfur-containing compound, it is preferred to use thiourea.

The halogenonitro-aromatic compounds which can be hydrogenated by the process of the present invention preferably correspond to the following formula:

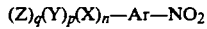
$(Z)_q(Y)_p(X)_n—Ar—NO_2$ wherein
Ar represents a monocyclic, polycyclic or heterocyclic aromatic radical which may or may not be fused and which may be substituted by an alkyl group containing 1 to 4 carbon atoms, X, Y and Z each independently represents a halogen selected from fluorine, chlorine and bromine,
n, p, and q each independently represents an integer of from 0 to 5, wherein the sum of n+p+q is greater than or equal to 1, and, preferably, is also less than or equal to 7.

It is preferred to use a monocyclic halogenonitro-aromatic compound containing 1 to 3 halogen atoms chosen from chlorine and/or fluorine fixed to the ring (e.g., q=0; n+p≧1 and ≦3), and more preferably the invention utilizes the following compounds:
chloronitrobenzenes
fluoronitrobenzenes
dichloronitrobenzenes
monochloro-monofluoro-nitrobenzenes
trichloronitrobenzenes
chloronitromethylbenzenes
fluoronitromethylbenzenes The hydrogenation of the halogenonitro-aromatic compounds with the aid of Raney nickel and the sulfur-containing agent can be carried out under customary hydrogenation conditions. Because of the high non-dehalogenation potential supplied by these sulfur-containing compounds, it is entirely possible to carry out the hydrogenation at a temperature of from 50° to 150° C. The hydrogenation is preferably carried out from 70° to 100° C., which enables productivities (amount of amine formed per hour and per volume of reaction mixture) to be obtained which are comparable with the productivities of non-halogenated amines.

Another advantage of the catalyst according to the invention, which was not provided by the catalysts deposited on charcoal, is the ease with which it can be used in continuous production processes. In fact, the separation of Raney nickel from the reaction mixture is clearly easier than that of the catalysts deposited on charcoal.

A final advantage of the catalyst according to the present invention is the ease with which it can be used; no prior preparation of the catalyst is necessary, as in French Patent 2,127,092 which requires hydrogenation of the catalyst followed by sulfurization. In the present process, it is necessary only to introduce all of the reagents into the hydrogenation reactor (the Raney nickel, the halogenonitro-aromatic compound, the sulfur-containing compound and, if utilized, the solvent) and then to pressurize the reactor with hydrogen.

The process of the invention can be carried out in the absence of solvent or in any solvent which is inert under the reaction conditions, such as, for example:
water (in the absence of a significant risk of hydrolysis, as is the case for monofluorinated compounds)
alcohols, such as methanol, ethanol or isopropanol and aromatic solvents, such as toluene or xylene
It is preferred to use methanol.

In an embodiment of the invention it is desirable to use an amount by weight of catalyst (nickel-, cobalt- or iron-based), and particularly Raney nickel, per liter of reaction mixture which is from 1 to 150 g and preferably from 5 to 50 g and an amount by weight of sulfur in the sulfur-containing compound, calculated relative to the nickel introduced, of from 0.2 to 10%. The higher quantity of sulfur-containing compound, in particular in the case of the sulfones and the sulfoxides, is desired. As will be seen further below, the sulfones and the sulfoxides can also serve as solvents.

In order to prevent hydrolysis, the amounts of sulfur compounds are advantageously larger than those necessary to inhibit the hydrogenolysis. The molar ratio between the sulfur compounds and the catalyst (nickel, cobalt or iron) advantageously ranges from about 1:1 to 10:1.

When the process is carried out continuously, the amount of halogenonitro-aromatic compound cannot be established in a static manner. Rather, a continuous process requires addition of this compound in the form of a flow. Thus, flow rates of about 1 to 3 moles per liter of reaction mixture, per hour, are fully recommended.

The hydrogen pressure is advantageously from 1 to 100 bars, more advantageously from 1 to 40 bars, preferably greater than 1 bar, more preferably from 5 to 25 bars, and most preferably from 20 to 25 bars.

When the present invention is used to treat the reaction mixtures resulting from the exchange between fluorine and a higher halogen, it is sufficient to add a nickel-based catalyst to the reaction mixture, after filtration, if necessary, to remove the salts of halo-hydric acids, and to conduct the hydrogenation reactions under the above conditions. The solvent will then be the same as that used during the exchange reaction, that is the solvents containing sulfur and oxygen. However, a dilution with a solvent which can be used during the hydrogenation, such as those cited above, may be employed.

Another aim of the present invention is to provide a new reagent for the hydrogenation of halogenated aromatic nitro derivatives, in particular for the synthesis of halogenated anilines, which prevents the hydrolysis and/or the hydrogenolysis of the carbon-halogen bonds.

This aim is achieved by a hydrogenation reagent containing:

a hydrogenation catalyst consisting essentially of a metal selected from nickel, cobalt and iron, advantageously nickel, preferably Raney nickel,
an organic solvent containing sulfur and oxygen; and
hydrogen, at a pressure preferably greater than 1 bar and more preferably from 5 to 25 bars.

An organic solvent containing sulfur and oxygen is any organic solvent which is inert towards the other constituents of the reagent and towards the substrates;
is liquid at the temperature at which the reaction takes place, advantageously has an initial melting point of below 100° C. and preferably has a finishing boiling point of higher than 100° C.; and
contains (at least) one —$SO_2$— or —SO— function in at least one of its main constituents when the solvent is a mixture.

Examples of organic solvents containing sulfur and oxygen are dimethyl sulfoxide (DMSO) and sulfolane.

As demonstrated in the results below, the use of sulfones and sulfoxides as solvents, or as a constituent element of the solvent, can lower the rate of hydrolysis and of hydrogenolysis, enabling the use of the crude reaction mixture originating from the halogen/fluorine exchange reaction when the solvent comprises sulfone(s) and/or sulfoxide(s) on its or their own or as a mixture with solvents which do not disturb the hydrogenation reaction.

The present invention will be described more completely with reference to the following examples, which in no case may be regarded as limiting the invention.

EXAMPLE 1

6 g of Raney nickel, 0.3 g of thiourea and 300 ml of 95% methanol were introduced into a 750 ml stainless steel autoclave. After closing, the reactor was purged several times with nitrogen and then with hydrogen.

The pressure was fixed at 20 bars. The reaction mixture was stirred and heated to a temperature of 100° C. Once this temperature was reached, 40 ml (377 mmoles) of the substrate (para-fluoronitrobenzene/ortho-fluoronitrobenzene mixture having a molar composition of 87%/13%) were introduced over the course of 22 minutes.

At the end of the reaction, the reactor was cooled to ambient temperature and then degassed.

The reaction mixture was filtered through a frit and the filtrate was analyzed by GPC (Gas Phase Chromatography).

The distribution of the products was as follows:

--- degree of conversion = 100%
para-fluoroaniline: 330.4 mmoles → yield = 87.6%
ortho-fluoroaniline: 47.7 mmoles → yield = 12.7%
aniline < 0.05%

---

The activity of the catalyst was 0.171 mole of substrate/g of nickel per h.

Comparative Example 1

The hydrogenation of the para-/ortho-fluoronitrobenzene mixture was carried out in the manner described in Example 1 (identical amounts), but without the addition of thiourea.

The distribution of products at the completion of the reaction was:

--- degree of conversion = 100%
para-fluoroaniline: 270 mmoles → yield = 71.6%
ortho-fluoroaniline: 27.6 mmoles → yield = 7.3%
aniline: 74.6 mmoles → yield = 19.8%
balance error = −1.3%

---

EXAMPLE 2

Hydrogenation of 3,4-dichloronitrobenzene

Starting Materials

90% MeOH = 100 ml
Raney Ni = 2 g
(additive): (see RESULTS)

Substrate dichloronitrobenzene: 25 g (130 mmoles)
dissolved in 125 cc of pure MeOH
(volume = 138 cc)

The solvent, the catalyst and, where appropriate, an additive or a neutralizing agent such as a buffer consisting of sodium acetate and acetic acid, were introduced into a 300 ml HASTELLOY autoclave. After closing, the reactor was purged several times with nitrogen and then with hydrogen and the pressure was fixed at 16.5 bars (this reached 18 bars at 75° C.). This mixture was stirred and heated to a temperature of 75° C. Once this temperature was reached, the substrate was injected over the course of 30 minutes. At the end of the reaction, the reactor was cooled to ambient temperature and then degassed.

The reaction mixture was filtered through a frit and the filtrate was analyzed by GPC.

RESULTS

| Raney Ni | Additive | Degree of conversion | Yield % 3-4 DCA | aniline | 3-ClA 4-ClA | Cl % molar |
|---|---|---|---|---|---|---|
| 2 g (20 g/l) | A$_c$OH: 0.8 g NaOH: 1.6 g | 100 | 90 | 6 | 3.5 | 15.6 |
| 2 g (20 g/l) | Thiourea: 0.1 g (1 g/l) | 100 | 99.3 | — | 0.3 | 0.4 |
| 2 g (20 g/l) | Na$_2$S.9 H$_2$O 0.325 g 3.25 g/l | 100 | 97.3 | 0.9 | 0.9 | 2.7 |

EXAMPLE 3

Hydrogenation of 3-Cl,4-F Nitrobenzene

The reaction was carried out in the manner described in Example 1, initially introducing

| | |
|---|---|
| MeOH (90%) = | 300 ml |
| Raney nickel = | 6 g |
| thiourea = | 0.9 g |
| and then, by injection | |
| 3-Cl, 4-F Nitrobenzene = (120 mmoles) | 21 g |

A hydrogen pressure of 20 bars was established and the reaction mixture was stirred and heated at 100° C.

After analysis by gas phase chromatography, it was shown that the conversion of 3-Cl,4-F Nitrobenzene was complete and that the hydrodechloration was 0.7%.

EXAMPLE 4

Synthesis of 2,4-difluoronitrobenzene

The following were charged into a 1 liter reactor, preheated to 50° C. and placed under a nitrogen atmosphere:
174 g of potassium fluoride (water content less than 100 ppm)
13 g of tetramethylammonium chloride
and 176 g of dimethyl sulfoxide (containing 50 ppm of water) and 230.4 g of 2,4-dichloronitrobenzene were then introduced.

The reaction mixture was stirred, so that all of the solid was in suspension, for 6 h at 130° C. The reactor was then cooled to 30° C. and the reaction mixture was diluted using 100 ml of methylene chloride. The mixture was stirred for 10 minutes and poured onto a glass frit. The reactor and the precipitate were rinsed twice with 100 ml of methylene chloride. The filtrate was recovered and the methylene chloride was evaporated using a rotary evaporator (bath=70° C., p=100 mmHg). 375.2 g of product were thus obtained: conversion 100%, yield of 2,4-difluoronitrobenzene 91% (purity 99%). This product was divided into three parts. The first (fraction A) was not purified further. The two other parts were washed with water to remove the DMSO.

The latter was recovered to the extent of 98% in the aqueous phase. The second part (fraction B) was used without further purification, while the third part (fraction C) was again purified by distillation.

EXAMPLE 5

Synthesis of 2,4-difluoronitrobenzene

The method described in Example 4 was repeated using, in a 1 liter reactor:
208.8 g of potassium fluoride (water content less than 100 ppm)
6 g of cesium fluoride
276.5 g of 2,4-dichloronitrobenzene and
215 g of sulfolane.

After heating for 11 h at 180° C., a conversion of 97.3% was obtained:

| | |
|---|---|
| yield of 2,4-difluoronitrobenzene = | 66.5% |
| yield of 2-fluoro-4-chloronitrobenzene = | 4.6% |
| yield of 4-fluoro-2-chloronitrobenzene = | 26.2% |

The crude reaction mixture was divided into two parts. The first (fraction D) was used without further purification. The second was further purified and resulted in a mixture of 69% 2,4-difluoronitrobenzene, 4.6% 2-fluoro-4-chloronitrobenzene and 26.4% 4-fluoro-2-chloronitro-benzene (fraction E).

EXAMPLE 6

0.18 g (3 mmoles) of Raney nickel, 15.2 g (15 mmoles) of 2,4-difluoronitrobenzene substrate (fraction A from example 4) and 15 ml of absolute ethanol were introduced into a 30 ml glass tube. The tube was placed in a 250 ml cylindrical autoclave, which was placed under a hydrogen atmosphere. The autoclave was stirred for 1 h 10 min at 60° C. under 20 bars of hydrogen. The aqueous solution obtained after traditional treatment was determined by GPC:
conversion 44.7%
selectivity for 2,4-difluoroaniline: 74.2%

EXAMPLES 7 TO 12

The method of Example 6 was repeated with the various fractions (cf. Examples 4 and 5) under the following conditions as shown in Table A.

TABLE A

| Ex. No. | Onium Substrate | Reaction Conditions | Time | Additional compound | Conversion of 24diFNB (%) | Yield of 24diFNB (%) |
|---|---|---|---|---|---|---|
| 7 | Fraction A | pH2-20 bars-60° C. | 3 h | — | 69.6 | 61.0 |
| 8 | Fraction B | pH$_2$-20 bars-60° C. | 1 h 10 mn | — | 75.7 | 70.1 |
| 9 | Fraction C | pH$_2$-20 bars-60° C. | 1 h 10 mn | — | 74.4 | 61.5 |
| 10 | Fraction C | pH2-20 bars-60° C. | 1 h 10 mn | DMSO-6% | 91.2 | 81.4 |

TABLE A-continued

| Ex. No. | Onium Substrate | Reaction Conditions | Time | Additional compound | Conversion of 24diFNB (%) | Yield of 24diFNB (%) |
|---|---|---|---|---|---|---|
| 11 | Fraction D | pH2-20 bars-60° C. | 1 h 10 mn | — | 47.9 | 75.9 |
| 12 | Fraction E | pH2-20 bars-60° C. | 1 h 10 mn | — | 69.7 | 63.4 |

EXAMPLE 13

The hydrogenation reaction was carried out by continuous addition of 80 mmoles of 2,4-difluoronitrobenzene (fraction A from Example 4), in a solution of 75 ml of ethanol, to a mixture containing 1 g of Raney nickel (16 mmoles) in 75 ml of ethanol at 60° C. under a hydrogen pressure of 20 bars.

The addition took place over a 4 h 40 min period. The following results were obtained:
conversion of 2,4-difluoronitrobenzene 100%
selectivity for 2,4-difluoroaniline 90%

Role of Sulfones and Sulfoxides in the Prevention of Hydrolysis

The analysis of the reaction mixtures after hydrogenation showed the very favorable role of these compounds used as solvent, in particular sulfoxides; the main results were collated in Table B.

TABLE B

| Ex. No. | Compound Containing Sulfur & Oxygen/Raney Ni (molar) | Degree of conversion (%) | Selectivity (%) of 24diFA | Yield (%) of F(OH)A |
|---|---|---|---|---|
| . | 10 | 69.6 | 89.8 | 2.8 |
| ? | 0 | 75.7 | 79.1 | 16.7 |
| 9 | 0 | 74.7 | 61.5 | 15.9 |
| 10 | 1 | 91.2 | 81.4 | 13.5 |
| 11 | 10 | 47.9 | 75.9 | 7.9 |
| 12 | 0 | 69.7 | 53.4 | 10.6 |
| 13 | 10 | 100 | 90 | 2 |

We claim:

1. A process for the preparation of a halogenoamino-homocyclicaromatic compound comprising the step of contacting a halogenonitro-homocyclicaromatic compound with hydrogen and hydrogenation catalyst consisting of a metal selected from the group consisting of nickel, cobalt and iron in the presence of a sulfur-containing compound selected from the group consisting of sulfides, organic sulfur-containing compounds and sulfites, at a temperature and hydrogen pressure sufficient to form said halogenoamino-homocyclicaromatic compound, wherein the amount by weight of sulfur in said sulfur-containing compound, calculated relative to the hydrogenation catalyst, is from 0.2 to 10%.

2. A process according to claim 1 wherein the catalyst is nickel.

3. A process according to claim 2 wherein said nickel is Raney nickel.

4. A process for the hydrogenation of halogenonitro-homocyclicaromatic compounds comprising the step of contacting in the presence or absence of a solvent a halogenonitro-homocyclicaromatic compound with hydrogen and a hydrogenation catalyst consisting of a metal selected from the group consisting of nickel, cobalt and iron, in the presence of a sulfur-containing compound selected from the group consisting of sulfides, organic sulfur-containing compounds and sulfites, at a temperature and hydrogen pressure sufficient to carry out said hydrogenation.

5. A process according to claim 4 wherein said sulfide is hydrogen sulfide and said sulfites are selected from hydrosulfites of alkali metals or ammonium which decompose to hydrogen sulfide in aqueous medium.

6. A process according to claim 4 wherein the catalyst is nickel.

7. A process according to claim 6 wherein said nickel is Raney nickel.

8. The process according to claim 1, wherein the halogenonitro-homocyclicaromatic compound corresponds to the formula:

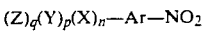

$(Z)_q(Y)_p(X)_n—Ar—NO_2$ wherein
Ar represents a monocyclic or polycyclic aromatic radical which may or may not be fused and may be substituted by an alkyl group containing 1 to 4 carbon atoms,
X, Y and Z each independently represents a halogen atom selected from fluorine, chlorine and bromine,
n, p, and q each independently represents an integer of from 0 to 5, wherein the sum of n+p+q is greater than or equal to 1.

9. The process according to claim 8, wherein Ar represents a monocyclic aromatic radical, X and Y represent chlorine and/or fluorine and the sum of n+p is greater than or equal to 1 and less than or equal to 3.

10. The process according to claim 1, wherein the halogenonitro-homocyclicaromatic compound is selected from chloronitrobenzenes, fluoronitrobenzenes, dichloronitrobenzenes, monochloro-monofluoro-nitrobenzenes, trichloronitrobenzenes, chloronitromethylbenzenes and fluoronitromethylbenzenes.

11. The process according to claim 4, wherein said sulfur-containing compound is selected from disulfides, thiophene, thioxane and thiourea.

12. The process according to claim 11, wherein said sulfur-containing compound is thiourea.

13. The process according to claim 4, wherein said hydrogenation is carried out in the absence of a solvent.

14. The process according to claim 4, wherein said hydrogenation is carried out in an inert solvent selected from water, alcohols and aromatic compounds.

15. The process according to claim 14, wherein said inert solvent is methanol.

16. The process according to claim 1, wherein the amount of said hydrogenation catalyst is from 1 to 150 g per liter of reaction mixture.

17. The process according to claim 16, wherein the amount of said hydrogenation catalyst is from 10 to 50 g per liter of reaction mixture.

18. The process according to claim 1, wherein the reaction temperature is from 50° C. to 150° C.

19. The process according to claim 18, wherein the reaction temperature is from 70° C. to 100° C.

20. The process according to claim 1, wherein the hydrogen pressure is from 1 to 100 bars.

21. The process according to claim 20, wherein the hydrogen pressure is from 1 to 40 bars.

22. The process according to claim 21, wherein the hydrogen pressure is from 5 to 25 bars.

23. The process according to claim 1 wherein said sulfur-containing compound is an organic solvent containing sulfur and oxygen.

24. The process according to claim 23, wherein said sulfur-containing compound is selected from sulfones and sulfoxides.

25. The process according to claim 24, wherein said sulfur-containing compound is selected from dimethylsulfoxide and sulfolane.

26. A process for the preparation of a halogenoamino-homocyclicaromatic compound comprising the step of contacting a halogenonitro-homocyclicaromatic compound with a reagent comprising a sulfur-containing compound selected from the group consisting of sulfides, organic sulfur-containing compounds and sulfites, hydrogen, and a hydrogenation catalyst consisting of a metal selected from the group consisting of nickel, cobalt and iron, wherein the amount of weight of sulfur in said sulfur-containing compound, calculated relative to the hydrogenation catalyst, is from 0.2 to 10%, and wherein the temperature and hydrogen pressure are sufficient to form said halogenoamino-homocyclicaromatic compound.

27. The process according to claim 24 wherein the molar ratio of said sulfur-containing compound to said catalyst ranges from about 1:1 to 10:1.

28. The process according to claim 26 wherein the sulfur-containing compound is selected from sulfones and sulfoxides and further wherein the molar ratio of said sulfur-containing compound to said catalyst ranges from about 1:1 to 10:1.

29. The process according to claim 1 wherein said sulfur-containing compound is thiourea.

* * * * *